US010646606B2

(12) United States Patent
Ditzler (10) Patent No.: US 10,646,606 B2
(45) Date of Patent: May 12, 2020

(54) OZONE CONCENTRATOR

(71) Applicant: Lee C Ditzler, Livermore, CA (US)

(72) Inventor: Lee C Ditzler, Livermore, CA (US)

(*) Notice: Subject to any disclaimer, the term of this patent is extended or adjusted under 35 U.S.C. 154(b) by 0 days.

(21) Appl. No.: 16/101,237

(22) Filed: Aug. 10, 2018

(65) Prior Publication Data

US 2019/0105417 A1    Apr. 11, 2019

Related U.S. Application Data

(63) Continuation of application No. 15/204,250, filed on Jul. 7, 2016, now Pat. No. 10,046,077.

(51) Int. Cl.
| | | |
|---|---|---|
| *B01F 3/04* | (2006.01) | |
| *A61L 2/18* | (2006.01) | |
| *B01F 5/04* | (2006.01) | |
| *B01F 15/00* | (2006.01) | |
| *A01N 59/00* | (2006.01) | |
| *B01F 5/10* | (2006.01) | |
| *A61L 2/24* | (2006.01) | |
| *A61L 2/22* | (2006.01) | |

(52) U.S. Cl.
CPC .............. *A61L 2/183* (2013.01); *A01N 59/00* (2013.01); *A61L 2/24* (2013.01); *B01F 3/0446* (2013.01); *B01F 3/04503* (2013.01); *B01F 5/0413* (2013.01); *B01F 5/0415* (2013.01); *B01F 5/106* (2013.01); *B01F 15/0022* (2013.01); *B01F 15/00344* (2013.01); *B01F 15/00993* (2013.01); *A61L 2/22* (2013.01); *A61L 2202/11* (2013.01); *A61L 2202/14* (2013.01); *B01F 2003/04886* (2013.01)

(58) Field of Classification Search
CPC ....... A61L 2/183; A01N 59/00; B01F 3/0446; B01F 5/0413; B01F 5/0415; B01F 15/0022; B01F 15/00344; B01F 15/00993
USPC .................................. 261/30, 76, 77, 119.1
See application file for complete search history.

(56) References Cited

U.S. PATENT DOCUMENTS

| | | | | |
|---|---|---|---|---|
| 6,482,370 | B2 * | 11/2002 | Holsclaw | A61L 2/183 204/176 |
| 6,598,431 | B2 * | 7/2003 | Teran | D06F 35/001 68/17 R |

\* cited by examiner

*Primary Examiner* — Robert A Hopkins
(74) *Attorney, Agent, or Firm* — West & Associates, A PC; Stuart James West; Theodore Marsh

(57) ABSTRACT

Systems and methods for dissolving ozone gas in a liquid. An embodiment can comprise a tank having an upper region, a lower region, and a discharge outlet, all disposed in a specified geometry. A pump can be coupled with a liquid inlet in order to receive a liquid therefrom and to deliver the liquid via a pipe to the upper region of the tank. The pump can be coupled with the lower region of the tank in order to receive the liquid from the tank and to recirculate the liquid to the upper region of the tank. The apparatus can include an ozone inlet to receive ozone into the tank. The ozone inlet can comprise a venturi inlet disposed on the pipe downstream of the pump. The liquid can be released from the tank and depressurized, thereby providing for the ozone to emerge from the liquid as gas bubbles. The released liquid can be selected for a two-stage gas and aqueous cleaning process.

8 Claims, 5 Drawing Sheets

OZONE CONCENTRATOR

CROSS REFERENCE TO RELATED APPLICATIONS

This Application is a continuation of co-pending U.S. patent application Ser. No. 15/204,250 filed Jul. 7, 2016, the entirety of which is hereby incorporated herein by reference.

TECHNICAL FIELD

The present disclosure relates to ozone concentrators

BACKGROUND

Water that contains dissolved ozone is known to be a good sanitizing agent. Such ozonated water can be used for washing fruits, vegetables, poultry, meat, containers, and the like. It can also be used to clean both the inside and outside of process equipment, such as washing process and bottling equipment, by hosing down the equipment with ozonated water and pumping ozonated water through the pumps, tanks, mixers, bottlers, and pipelines. The length of time required for a specific sanitization level can be inversely related to the concentration of dissolved ozone in the water. That is, the higher the concentration of ozone in the water, the shorter the length of time required for a particular sanitization level to be achieved. Some conventional sanitizing systems have been able to achieve ozonated water of only approximately 2-4 ppm of dissolved ozone.

SUMMARY

Implementations may include one or more of the following features. The system: where the ozone inlet includes a venturi inlet disposed on the pipe downstream of the pump. The system: where the pump is configured to pump the liquid at a sufficient pressure to produce a vacuum at the venturi inlet, thereby drawing at least some of the ozone into the pipe. The system further including: a pressure regulator disposed between the liquid inlet and the pump; where the pressure regulator is configured to regulate pressure of the liquid; and, where the sufficient pressure is adequate to overcome a regulated pressure set by the pressure regulator. The system further including: a static mixer coupled with the pipe and disposed downstream of the ozone inlet and upstream of the tank. The system further including: a degas valve coupled with the tank and configured to release gas from the tank. The system further including: an inlet tube coupled between the liquid inlet and the pump, the inlet tube disposed in the lower region of the tank; where the inlet tube includes at least one aperture configured to extract liquid from the tank, thereby recirculating the liquid via the pipe to the tank. The system further including: an exit outlet coupled with the tank; where the system is configured to deliver the liquid to the upper region of the tank at a location spaced from the exit outlet, thereby providing a contact time for dissolving ozone in the liquid and degassing the liquid. The system further including: a valve disposed between the liquid inlet and the pump. The system further including: an exit outlet coupled with the tank, where the tank is configured to maintain a pressure higher than an ambient pressure outside the tank and proximate to the exit outlet. The system further including: an ozone monitoring system coupled with the tank and configured to provide a measurement of dissolved ozone within the tank, and, provide a control signal responsive to the measurement; and, an ozone generator coupled with the ozone inlet and configured to receive the control signal, and, provide the ozone responsive to the control signal. The method: where the ozone is introduced into the flow of the liquid via a venturi inlet, and, the venturi inlet is on the pipe. The method further including the step of: pumping the flow of the liquid at a sufficient pressure, thereby producing a vacuum at the venturi inlet; where the vacuum is sufficient to draw at least some of the ozone into the pipe. The method further including the step of: providing a release rate for releasing the liquid from the tank, where the liquid is recirculated at a recirculation rate within a range of 1 to 6 times the release rate. The method further including the steps of: measuring dissolved ozone within the tank, thereby providing a measurement; providing a control signal responsive to the measurement; and, generating the ozone responsive to the control signal. The method further including the step of: receiving the flow of the liquid into the tank at a distance from an exit outlet, thereby providing a contact time for dissolving ozone in the liquid and degassing the liquid. The method further including the steps of: measuring dissolved ozone within the tank, thereby providing a measurement; providing a control signal responsive to the measurement; and, generating the ozone responsive to the control signal. Implementations of the described techniques may include hardware, a method or process, or computer software on a computer-accessible medium.

One general aspect includes a method of dissolving ozone in a liquid, including the steps of: introducing ozone into a flow of a liquid in a pipe into a tank; recirculating at least a portion of the liquid from the tank via the pipe into the tank; and, releasing the liquid from the tank, thereby depressurizing the liquid (in some embodiments at the nozzle or exit outlet 140) and providing for at least some of the ozone to emerge from the liquid as gas bubbles. Other embodiments of this aspect include corresponding computer systems, apparatus, and computer programs recorded on one or more computer storage devices, each configured to perform the actions of the methods.

Implementations may include one or more of the following features. The method: where the ozone is introduced into the flow of the liquid via a venturi inlet, and, the venturi inlet is on the pipe. The method further including the step of: pumping the flow of the liquid at a sufficient pressure, thereby producing a vacuum at the venturi inlet; where the vacuum is sufficient to draw at least some of the ozone into the pipe. The method further including the step of: providing a release rate for releasing the liquid from the tank, where the liquid is recirculated at a recirculation rate within a range of 1 to 6 times the release rate. The method further including the steps of: measuring dissolved ozone within the tank, thereby providing a measurement; providing a control signal responsive to the measurement; and, generating the ozone responsive to the control signal. The method further including the step of: receiving the flow of the liquid into the tank at a distance from an exit outlet, thereby providing a contact time for dissolving ozone in the liquid and degassing the liquid. The method further including the steps of: measuring dissolved ozone within the tank, thereby providing a measurement; providing a control signal responsive to the measurement; and, generating the ozone responsive to the control signal. Implementations of the described techniques may include hardware, a method or process, or computer software on a computer-accessible medium.

One general aspect includes a method of dissolving ozone in a liquid, including the steps of: providing a flow of a liquid in a pipe into a tank; introducing ozone into the flow of the liquid via a venturi inlet, where the venturi inlet is on the pipe; pumping the flow of the liquid at a sufficient pressure, thereby producing a vacuum at the venturi inlet; and, recirculating at least a portion of the liquid from the tank via the pipe into the tank; where the vacuum is sufficient to draw at least some of the ozone into the pipe. Other embodiments of this aspect include corresponding computer systems, apparatus, and computer programs recorded on one or more computer storage devices, each configured to perform the actions of the methods.

Implementations may include one or more of the following features. The method further including the step of: receiving the flow of the liquid into the tank at a distance from an exit outlet, thereby providing a contact time for dissolving ozone in the liquid and degassing the liquid. The method further including the steps of: measuring dissolved ozone within the tank, thereby providing a measurement; providing a control signal responsive to the measurement; and, generating the ozone responsive to the control signal. Implementations of the described techniques may include hardware, a method or process, or computer software on a computer-accessible medium.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a system for dissolving ozone in a liquid, including: a tank including an upper region, a lower region coupled with the upper region, and a discharge outlet disposed between the upper region and the lower region; a pipe coupled with the tank and the discharge outlet; a liquid inlet configured to provide a liquid; a pump coupled with the pipe and the liquid inlet and configured to receive the liquid from the liquid inlet, and, deliver the liquid via the pipe to the upper region; and, an ozone inlet coupled with the pipe and configured to receive ozone, thereby providing ozone to the tank. Other embodiments of this aspect include corresponding computer systems, apparatus, and computer programs recorded on one or more computer storage devices, each configured to perform the actions of the methods.

DETAILED DESCRIPTION

Figure 1:
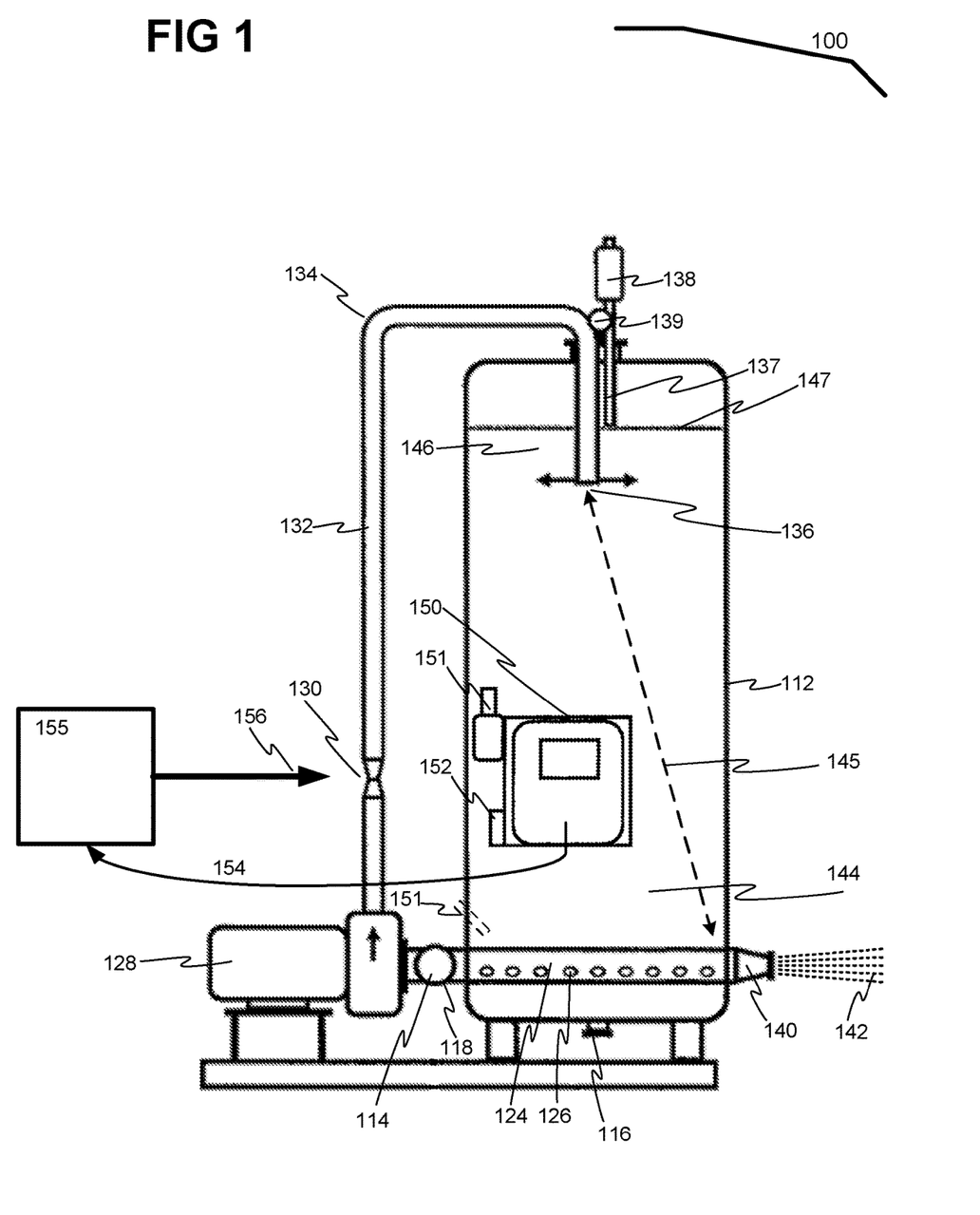
FIG. 1 depicts an elevation view of an ozone concentrator system.

Diagram 100 depicts some embodiments of an apparatus for dissolving ozone in a liquid. An apparatus comprises a tank 112 having an upper region 146, a lower region 144, and a discharge outlet 136, all disposed in a specific geometry. In some embodiments, the discharge outlet 136 can be disposed between the upper region 146 and the lower region 144. In other embodiments, the upper 146 and lower 144 regions and discharge outlet 136 can be arranged in any known and/or convenient geometry. A pump 128 can be coupled with a liquid inlet 114 to receive a liquid 110 therefrom and to deliver the liquid via a pipe 134 to the upper region 146 of the tank 112. Liquid 110 can be within many elements of the system 100, such as tank 112, pipe 134, pump 128, and inlet tube 124. Liquid is shown as filling tank 112 to water level 147. The pump 128 can be coupled with the lower region 144 of the tank in order to receive the liquid from the tank 112 and to recirculate the liquid to the upper region 146 of the tank 112. An ozone inlet 130 can be provided, in order to receive ozone 156 into the tank 112.

In some embodiments, the ozone inlet 130 comprises a venturi inlet disposed on the pipe 134 downstream of the pump 128. A pressure regulator 118 can be disposed between the liquid inlet 114 and the pump 128 in order to regulate the pressure of the liquid in the tank 112. The pump 128 can be configured to pump the liquid at a sufficient pressure to produce a vacuum at the venturi inlet 130, thereby drawing ozone 156 into the pipe 134. A static mixer 132 can be disposed downstream of the ozone inlet 130 and upstream of the tank 112. A degas valve 138 can be provided for releasing gas from the tank 112. Liquid can be desirably delivered to the upper region 146 of the tank at a location spaced 145 from an exit outlet 140. This distance 145 can provide for a corresponding contact time for dissolving ozone in the liquid and degassing the liquid.

Some method embodiments for dissolving ozone in a liquid can comprise introducing ozone 156 into a flow of a liquid 110 in a pipe 134 into a tank 112, and recirculating at least a portion of the liquid from the tank 112 via the pipe 134 into the tank. Liquid can be released from the tank and depressurized (in some embodiments at the nozzle or exit outlet 140), thereby causing ozone to emerge from the ozonated liquid 142 as gas bubbles. This emergence of the gas can cause surface agitation and surface sanitizing by the ozone gas and the ozonated liquid, thus providing for a two-stage gas and aqueous cleaning regimen. In some embodiments, ozone 156 can be introduced into the flow of liquid via a venturi inlet 130 provided on the pipe 134. A release rate for releasing liquid from the tank can be provided. In some embodiments, liquid can be recirculated at a recirculation rate in a range of 1-6 times the release rate Some method embodiments for dissolving ozone 156 in a liquid comprise providing a flow of a liquid 110 in a pipe 134 into a tank, and pumping the flow of liquid. Ozone 156 can be introduced into the flow of the liquid via a venturi inlet 130 provided on the pipe 134. The flow of liquid can be pumped at a sufficient pressure to produce a vacuum at the venturi inlet 130, thereby drawing the ozone 156 into the pipe 134. Liquid can be recirculated from the tank 112 via the pipe 134 into the tank 112.

Some embodiments of systems and methods as disclosed herein can provide ozonated water having dissolved ozone levels of 10 ppm and higher. This can be accomplished by a system that introduces ozone 156 into water which is under pressure, circulates the water to dissolve the ozone therein at a higher concentration, and releases the pressurized ozonated water 142. In some embodiments, the system can create large quantities of very small bubbles as the ozonated water becomes depressurized during release. Solubilized gases, including ozone, can come out of the depressurized ozonated water 142 solution, thereby providing the small and/or micro bubbles. The bubbles can create surface agitation and can provide direct ozone gas contact with the surfaces being treated. This can provide a two-stage gas and aqueous cleaning regimen that can be effective for sanitizing surfaces. Such a two-stage cleaning regimen can be advantageously employed for treating some surfaces that are difficult to clean using only ozonated water. Some embodiments can be employed to treat water containing contaminating chemicals such as MTBE, TCE, PCE, or the like. A high concentration of ozone, such as provided by these embodiments, can advantageously provide relatively faster and/or more complete oxidation of such contaminants.

Figure 2:
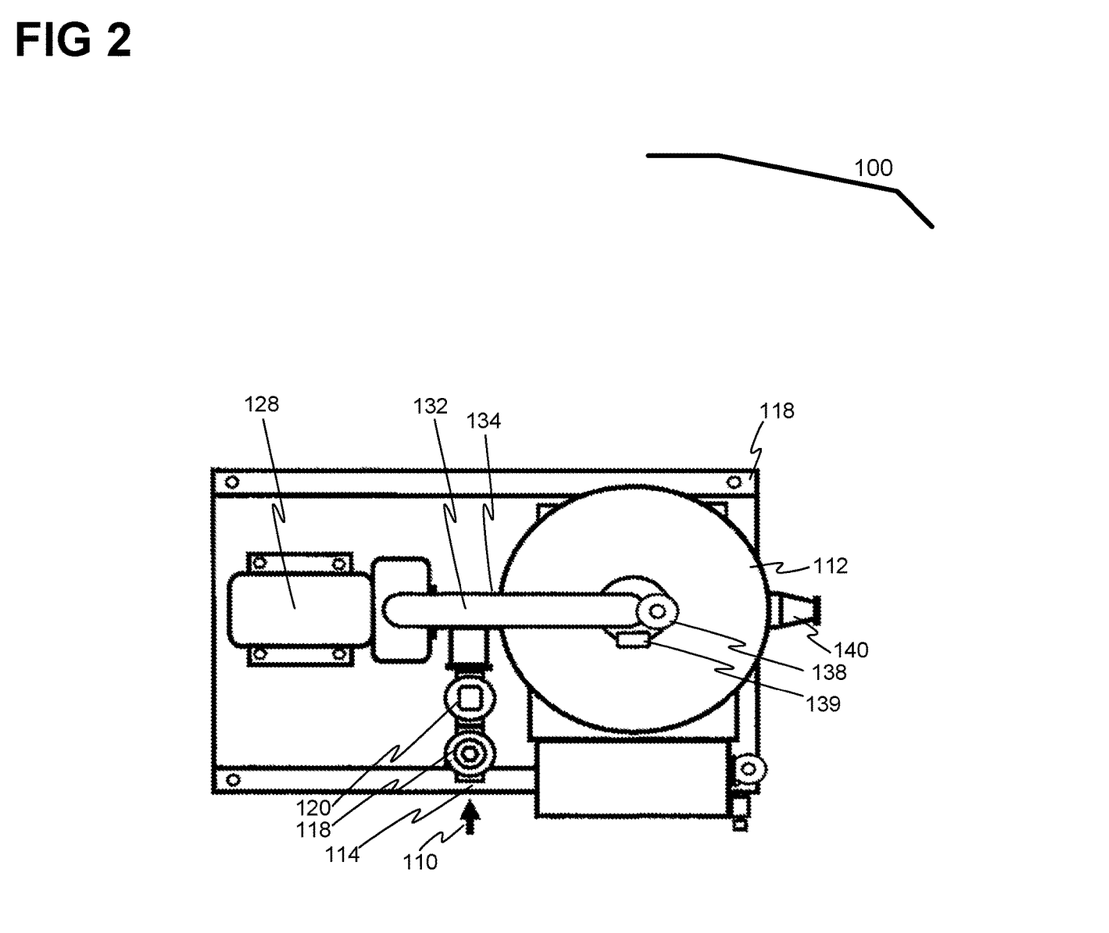
FIG. 2 depicts a top plan view of an ozone concentrator system.

As shown in FIGS. 1 and 2, a system embodiment 100 for producing ozonated water having a high ozone concentration comprises a tank 112. Incoming water 110 can enter a water inlet 114, and desirably pass through a pressure regulator 118, and a valve 120. In some embodiments, any known and/or convenient pressure regulator and/or valve can be employed. In some embodiments, the valve 120 can be a solenoid valve. The water can flow through an inlet tube 124 which can be desirably disposed in a lower region 144 of the tank 112. In some embodiments, the inlet tube 124 can be disposed proximate to the bottom of the tank 112. The inlet tube 124 can include one or more apertures 126. A pump 128 can be coupled to the inlet tube 124 to pump water from the lower region 144 to an upper region 146 of the tank 112 via a pipe 134. Such a recirculating pump 128 can draw incoming water from the inlet 114, and can also extract and recirculate water in the tank 112 which enters the inlet tube 124 through the apertures 126. The water can pass through an ozone inlet 130 and a static mixer 132 downstream of the pump 128. In some embodiments, the ozone inlet 130 can be a venturi eductor, and can be referred to herein as a venturi ozone inlet and/or a venturi inlet. Ozone 156 can be added to the water under negative pressure via the venturi ozone inlet 130 and mixed with the water in the static mixer 132. In some embodiments, such ozone can be provided by an ozone generator 155. The water can pass through a discharge outlet 136 in an upper region 146 of the tank 112. Via the discharge 136, such water can enter the tank 112 below a water level 147 of the tank 112. In some embodiments, the water can enter the tank 112 12 inches below the water level 147. However, in alternate embodiment any desired distance below the water level 147 of the tank 112 can be used. A degas valve 138 and a pressure gauge 139 can be provided, and disposed at and/or proximate to the top of the tank 112.

The apparatus 100 can comprise a skid and/or support upon which tank 112 and pump 128 can be mounted. Tank 112 can comprise a drain fitting 116. In some embodiments, waste products from operation of the apparatus can emanate from drain fitting 116. Examples of such waste products can comprise outputs of a degas valve 138 and/or sampled water output of an ozone monitoring system 150.

In operation, water can flow from the upper region 146 to the lower region 144 of the tank 112. An ozonated water exit outlet 140, also described herein alternatively as an exit outlet and/or a water outlet and/or an ozonated water outlet, can be provided for ozonated water 142 to exit the tank 112. The exit outlet 140 can be disposed at an end of the inlet tube 124. Another, opposite end of the inlet tube 124 can be disposed proximate to the pump 128. Upon exiting the tank 112, the ozonated water 142 can be used for processing such as sanitizing and washing. The exit outlet 140 can be desirably disposed closer to the bottom than the top of the tank 112, that is, within the lower region 144. The exit outlet 140 can be disposed at a distance 145 from the discharge 136 that corresponds to providing adequate contact time for the water, and providing for degassing the water prior to the water exiting the tank 112.

In such embodiments, incoming water can enter the inlet tube 124 in the lower region 144 proximate to the bottom of the tank 112, can be drawn by the pump 128 and ozonated prior to entering the tank 112 proximate to the top of the tank 112, and can exit at the exit outlet 140. Thus incoming water 110 can be ozonated prior to entering the tank 112, and degassed and ozonated water can exit the tank 112 via exit outlet 140 before reaching the inlet tube 124. A specific contact time can be determined, with dependencies comprising a desired ozone concentration and/or process conditions such as temperature and pressure. In some typical embodiments, tank pressure can be maintained at a pressure higher than an ambient pressure, such as an ambient pressure found just outside the tank 112 and proximate to the exit outlet 140.

By recirculating water through the tank 112, a higher concentration, that is, a higher dissolved ozone level, can be achieved. The venturi ozone inlet 130 can facilitate introduction of ozone 156 into the pressurized water. The pump 128 can preferably deliver water at a sufficient pressure to overcome the regulated pressure of the incoming water as set by the pressure regulator 118, thereby producing a vacuum at the venturi ozone inlet 130 sufficient to draw in the ozone 156. In some embodiments, the pump 128 can be desirably sized to recirculate at least approximately twice the maximum amount of water that can be delivered through exit outlet 140. That is, the water recirculation rate can be at least two times a specific water release rate. In some embodiments, the recirculation rate can be within a range of approximately 1-6 times the release rate. In some specific embodiments, the recirculation rate can be about 2 times the release rate. In other embodiments the recirculation rate can be any convenient and/or desired rate.

Tank 112 can have a variety of shapes and sizes. In some typical embodiments, the tank 112 can be circular cylindrical, and can have a height to diameter ratio of about 1-50. In some embodiments, the height to diameter ratio can be about 5. In other embodiments, the height to diameter ratio can be any convenient and/or desired ratio. The tank 112 can be desirably sized to a specific pump flow.

By way of non-limiting example, in some embodiments a 100 gallon tank with a two times turnover rate can require a 200 gallon pump. In other embodiments, the tank volume can vary from about 1 to 20 times the pump flow. In a specific embodiment, the tank volume can be sized to provide about 60 seconds retention or contact time. In such an embodiment, the retention time can vary, for example, from about 2 seconds to about 60 minutes.

A degas valve 138 can release gasses from the tank 112, such as air and/or oxygen that are not converted to ozone by the ozone generator. In some embodiments a degas valve 138 can comprise a small orifice having a size of, for example, about 0.02 to 0.25 inch. A small orifice can ensure that pressure is maintained in the tank 112 while the degas valve 138 is open. The size of the orifice can vary with the size of the tank 112 and the amount of gas to be released. In some embodiments, the degas valve 138 can desirably comprise a float which can maintain the water level to within a few inches of the top of the tank 112. The float can move upward to close the orifice, and can drop to release or bleed off gas using a dip pipe 137 to maintain a water level 147. In some embodiments, the degas valve 138 can maintain the water level to any convenient and/or desirable level with respect to the geometry of the tank 112. In some embodiments, degas valve 138 can comprise any known and/or convenient mechanism for desirably releasing gasses from tank 112.

In operation under the condition of no water exiting through the exit outlet 140, the pump 128 can continuously recirculate the water in the tank 112. The contact tank 112 can operate at a pressure that can be set by the incoming pressure regulator 118. A pressure gauge 139 can provide an indication of the operating pressure.

In operation of an embodiment, upon the system being turned on, the valve 120 opens and the pump 128 operates. Upon the system being turned off, the valve 120 closes and the pump 128 is deactivated. In one embodiment, the pump 128 and valve 120 can be connected to a common power source. The inlet valve 120 can advantageously prevent the tank 112 from being pressurized when the system is not operating. In some embodiments, valve 120 can be a solenoid valve. In other embodiments, valve 120 can be any known and/or convenient valve with desirable operating characteristics.

An operating pressure can be set to any desired level. In operation of some typical embodiments, it can be set to about 5-200 psi. Per Henry's gas law, solubility of ozone varies directly with gas pressure. Thus, in some embodiments, it can be desirable to provide increased gas pressure in order to increase the concentration of dissolved ozone in the fluid.

In operation of some embodiments, a pressure of about 40 ppm psi can typically be sufficient to operate spray wash applications. The ozonated water 142 exiting the outlet 140 can be delivered to an application device such as a spray wash nozzle, thereby reducing the pressure to ambient. The reduction in pressure can cause ozone gas to emerge from solution in the form of gas bubbles. Such gas bubbles can be of microscopic size. In some applications, surface agitation and surface sanitizing as provided by the ozone gas and ozonated water can provide a two-stage gas and aqueous cleaning effect. Such two-stage cleaning can reduce cleaning time, and can be capable of sanitizing surfaces that are difficult to clean using only ozonated water. The time reduction can provide a significant benefit in many applications.

When treating water that contains chemicals, the very high levels of dissolved ozone obtainable using the present system can provide a more rapid treatment than that provided by low ozone concentrations. Advanced oxidation involving ozone with hydrogen peroxide can also be employed in conjunction with the present system in order to produce effective treatments. In some such embodiments, hydrogen peroxide can be added to the suction of the venturi eductor inlet 130. A tank volume can be determined and/or selected in order to provide sufficient treatment or contact time to oxidize the contaminants. Such a sufficient treatment time can vary based on the type of contaminants and the amount of contaminants.

Figure 3:
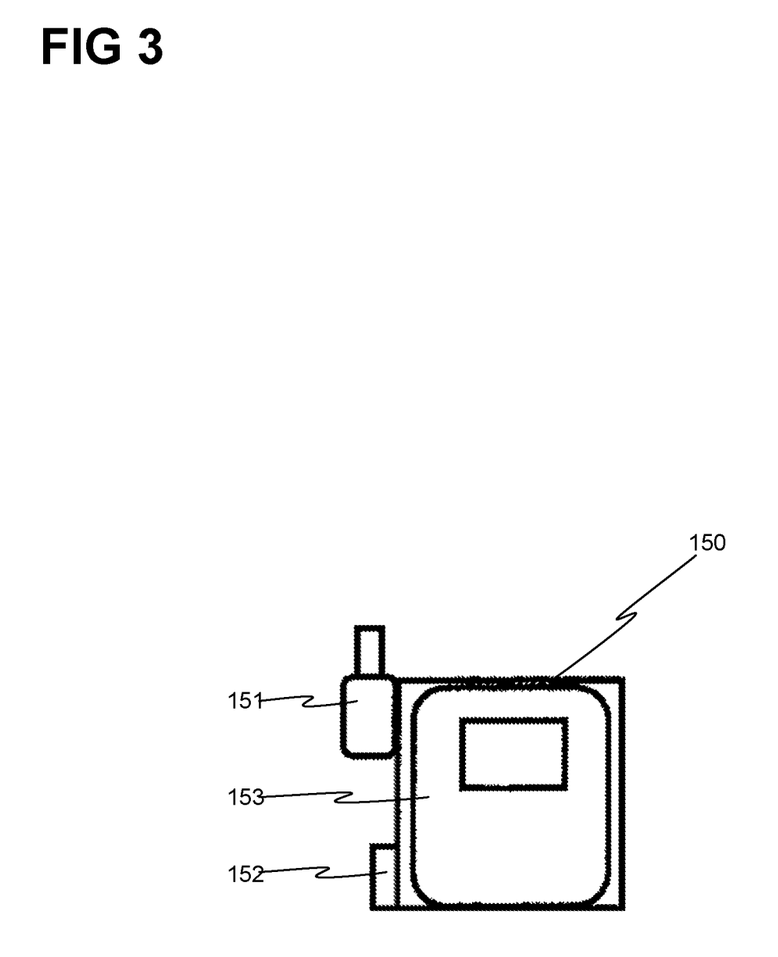
FIG. 3 depicts an ozone monitoring system.

Some system embodiments can further comprise an ozone monitoring system 150. FIG. 3 depicts details of such a system. A measurement of dissolved ozone can be provided by an ozone monitoring system 150 comprising a dissolved ozone probe 151, a rotometer 152 that can measure and control the sample flow, and a dissolved ozone monitor 153. The ozone monitoring system 150 can be coupled with the tank 112, thereby providing the monitoring system with access to liquid within the tank. Sample of liquid from within the tank 112 can be taken at or near the ozonated exit outlet 140 and discharged to waste after flowing past the dissolved ozone probe 151. In some embodiments, the probe 151 can pass directly through the tank 112. In some embodiments in which the probe 151 passes directly through the tank 112, the probe 151 can pass through the tank at an angle, such as, by way on non-limiting example, 45 degrees relative to the side of the tank 112. However in alternate embodiments in which the probe 151 passes directly through the tank 112, the probe 151 can pass through the tank 112 at any known, convenient and/or desired angle relative to the side of the tank 112. The ozone monitor 153 can provide an output signal 154. The output signal 154 can be a control signal responsive to the measurement of dissolved ozone and a desired level of dissolved ozone. In some embodiments, the output signal 154 can be in a range of 4-20 ma, and can be employed as feedback to an ozone generator 155. In other embodiments, the output signal 154 voltage or other signaling characteristic can be in any known and/or convenient range, and can correspond to any known and/or convenient range of dissolved ozone. Automatic dosage control for the ozone generator 155 can be responsive to such feedback. That is, ozone generator 155 can provide ozone 156, responsive to the ozone monitor 153 output signal 154 received by the ozone generator 155. In some typical embodiments, a dissolved ozone signal of 4 to 20 ma can correspond respectively to a range of 0 to 10 ppm of dissolved ozone. In other embodiments, the signal range can correspond to a range of 0 to 1 ppm of dissolved ozone, or a range of 0 to 20 ppm of dissolved ozone. In yet other embodiments, the signal range can correspond to any known and/or convenient range of dissolved ozone.

Figure 4:
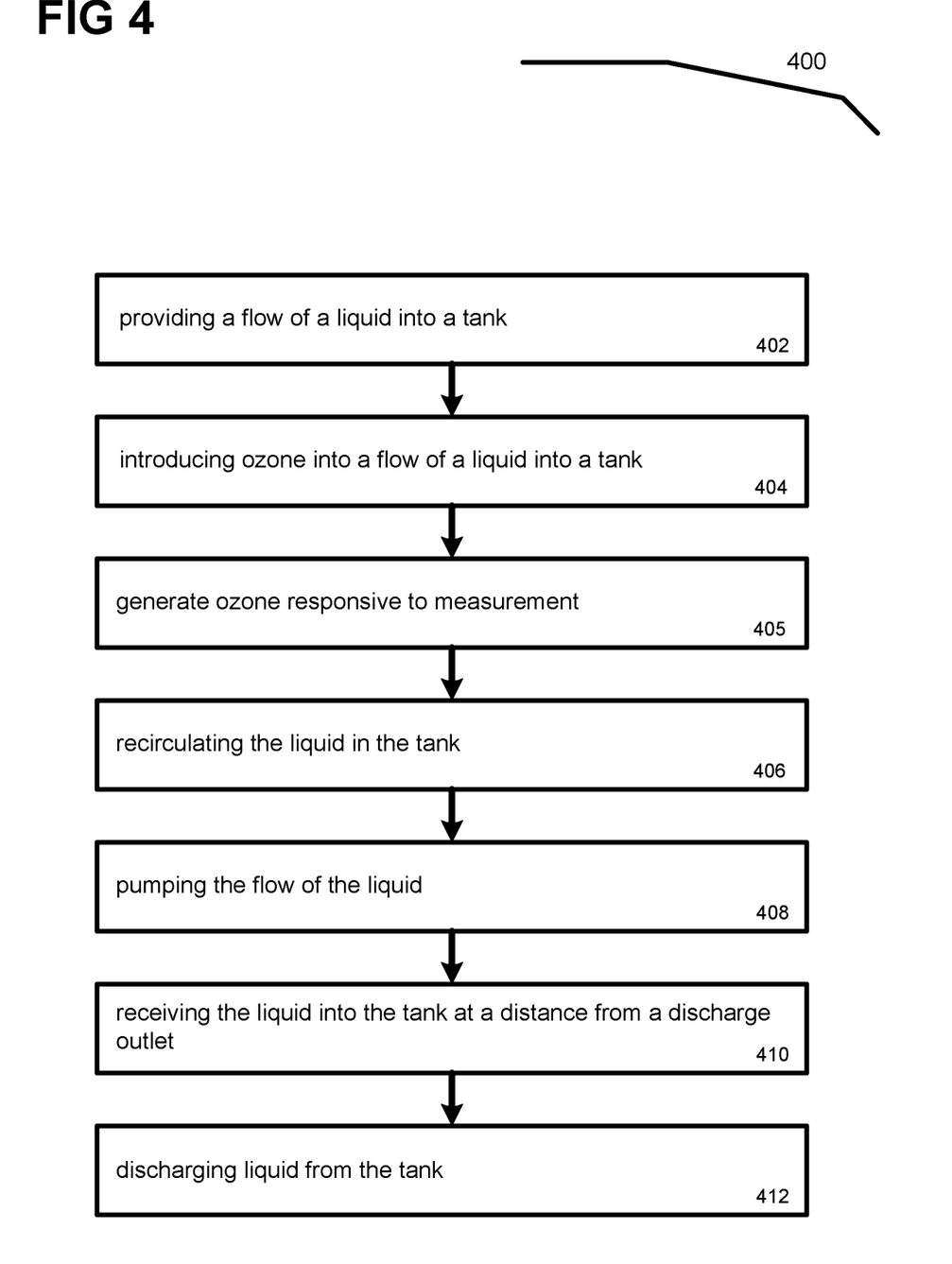
FIG. 4 depicts a method for dissolving ozone in a liquid.

Diagram 400 of FIG. 4 depicts steps of a method for dissolving ozone in a liquid. Although some descriptions herein characterize the liquid as water, the embodiments are not so limited. Other liquids, such as by way of non-limiting examples, oils, can be employed.

In step 402, a flow of a liquid into a tank is provided. In diagram 100, pipe 134 provides for such a flow into tank 112.

In step 404, ozone 156 can be introduced into a flow of a liquid into a tank. In diagram 100, ozone inlet 130 (also described as a venturi inlet and/or a venture eductor) provides for introduction of ozone into pipe 134 and thereby into the flow of the liquid into the tank 112.

In step 405, the ozone 156 can be generated responsive to a measurement of dissolved ozone within liquid in the tank 112. An ozone monitoring system 150 can provide the measurement. The monitoring system 150 can provide a control signal 154 responsive to the measurement and a desired level of dissolved ozone within the liquid within the tank 112. An ozone generator 155 can generate ozone 156 responsive to the control signal 154.

In step 406, liquid in the tank 112 can be recirculated. In diagram 100, liquid can circulate and recirculate in a specific path. Liquid can enter inlet tube 124 through one or more apertures 126, and be drawn towards pump 128 by the action of the pump 128. The liquid can flow through pipe 134 and be discharged into an upper region 146 of the tank 112. The liquid can flow from discharge 136 through the tank and to the inlet tube 124 apertures 126, thus recirculating. In some embodiments, the liquid can be recirculated at a rate within a range of 1 to 6 times a release rate for releasing liquid from the tank 112. Diagram 100 depicts the liquid ozonated water 142 released from the tank 112 via exit outlet 140.

In step 408, the flow of the liquid can be pumped. In diagram 100, pump 128 can pump the liquid at a pressure sufficient to produce a vacuum at the venturi inlet 130. The vacuum at the venturi inlet 130 can be sufficient to draw some ozone into pipe 134 at the inlet 130.

In step 410, liquid can be received into the tank at a distance from an exit outlet. In diagram 100, liquid can be received into the tank 112 at discharge 136, with discharge 136 spaced at a distance 145 to exit outlet 140. The distance 145 corresponds to providing a contact time during which ozone can dissolve into the liquid, and during which contact time the liquid can become degassed.

In step 412, liquid can be released from the tank. In diagram 100, ozonated water 142 can be released from the tank via exit outlet 140. The released ozonated water 142 can thereby be depressurized, providing for ozone to emerge from the liquid. Ozone can emerge from the liquid as gas bubbles.

Figure 5:
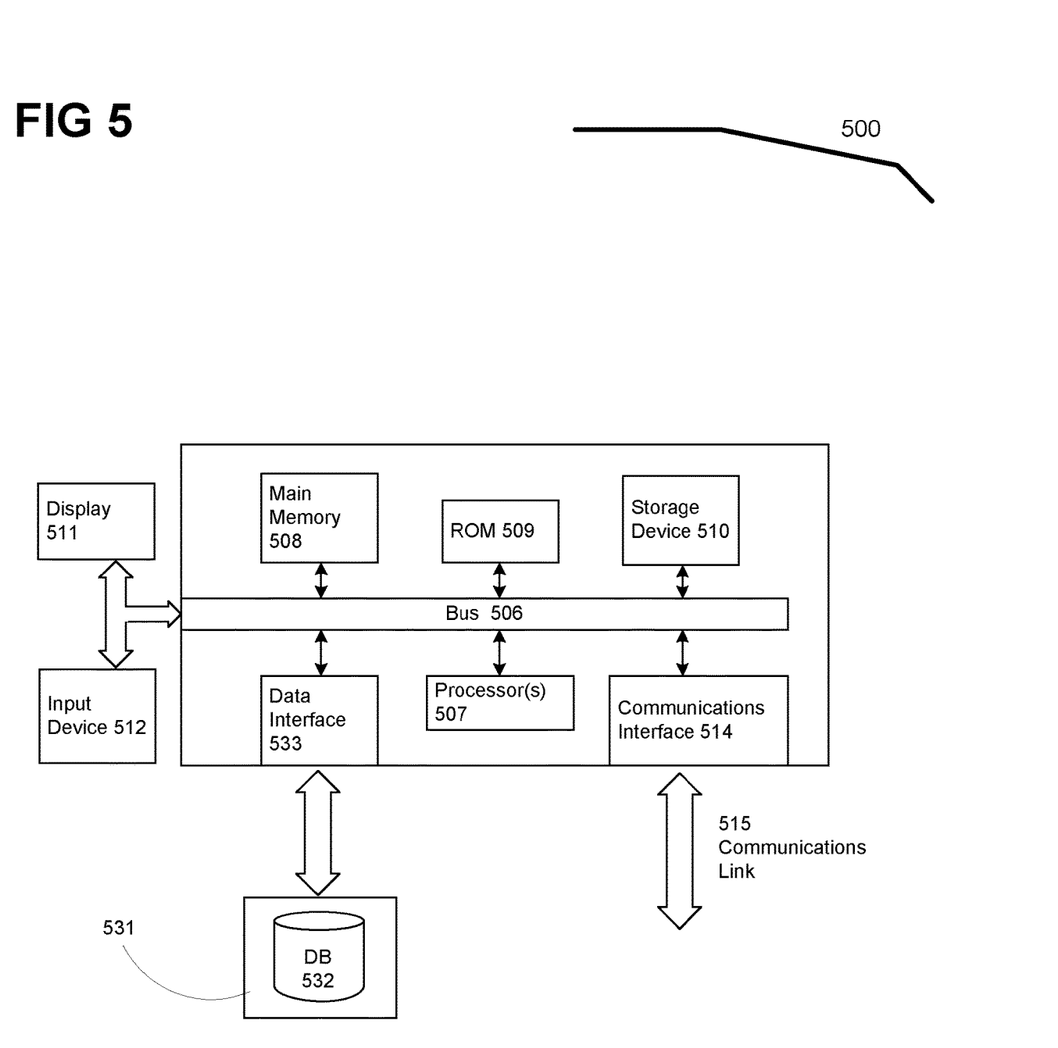
FIG. 5 depicts a computer system.

The execution of the sequences of instructions required to practice the embodiments can be performed by a computer system 500 as shown in FIG. 5. In an embodiment, execution of the sequences of instructions is performed by a single computer system 500. According to other embodiments, two or more computer systems 500 coupled by a communication link 515 can perform the sequence of instructions in coordination with one another. Although a description of only one computer system 500 will be presented below, however, it should be understood that any number of computer systems 500 can be employed to practice the embodiments.

A computer system 500 according to an embodiment will now be described with reference to FIG. 5, which is a block diagram of the functional components of a computer system 500. As used herein, the term computer system 500 is broadly used to describe any computing device that can store and independently run one or more programs.

Each computer system 500 can include a communication interface 514 coupled to the bus 506. The communication interface 514 provides two-way communication between computer systems 500. The communication interface 514 of a respective computer system 500 transmits and receives electrical, electromagnetic or optical signals, that include data streams representing various types of signal information, e.g., instructions, messages and data. A communication link 515 links one computer system 500 with another computer system 500. For example, the communication link 515 can be a LAN, in which case the communication interface 514 can be a LAN card, or the communication link 515 can be a PSTN, in which case the communication interface 514 can be an integrated services digital network (ISDN) card or a modem, or the communication link 515 can be the Internet, in which case the communication interface 514 can be a dial-up, cable or wireless modem.

A computer system 500 can transmit and receive messages, data, and instructions, including program, i.e., application, code, through its respective communication link 515 and communication interface 514. Received program code can be executed by the respective processor(s) 507 as it is received, and/or stored in the storage device 510, or other associated non-volatile media, for later execution.

In an embodiment, the computer system 500 operates in conjunction with a data storage system 531, e.g., a data storage system 531 that contains a database 532 that is readily accessible by the computer system 500. The computer system 500 communicates with the data storage system 531 through a data interface 533. A data interface 533, which is coupled to the bus 506, transmits and receives electrical, electromagnetic or optical signals, that include data streams representing various types of signal information, e.g., instructions, messages and data. In embodiments, the functions of the data interface 533 can be performed by the communication interface 514.

Computer system 500 includes a bus 506 or other communication mechanism for communicating instructions, messages and data, collectively, information, and one or more processors 507 coupled with the bus 506 for processing information. Computer system 500 also includes a main memory 508, such as a random access memory (RAM) or other dynamic storage device, coupled to the bus 506 for storing dynamic data and instructions to be executed by the processor(s) 507. The main memory 508 also can be used for storing temporary data, i.e., variables, or other intermediate information during execution of instructions by the processor(s) 507.

The computer system 500 can further include a read only memory (ROM) 509 or other static storage device coupled to the bus 506 for storing static data and instructions for the processor(s) 507. A storage device 510, such as a magnetic disk or optical disk, can also be provided and coupled to the bus 506 for storing data and instructions for the processor(s) 507.

A computer system 500 can be coupled via the bus 506 to a display device 511, such as, but not limited to, a cathode ray tube (CRT) or a liquid-crystal display (LCD) monitor, for displaying information to a user. An input device 512, e.g., alphanumeric and other keys, is coupled to the bus 506 for communicating information and command selections to the processor(s) 507.

According to one embodiment, an individual computer system 500 performs specific operations by their respective processor(s) 507 executing one or more sequences of one or more instructions contained in the main memory 508. Such instructions can be read into the main memory 508 from another computer-usable medium, such as the ROM 509 or the storage device 510. Execution of the sequences of instructions contained in the main memory 508 causes the processor(s) 507 to perform the processes described herein. In alternative embodiments, hard-wired circuitry can be used in place of or in combination with software instructions. Thus, embodiments are not limited to any specific combination of hardware circuitry and/or software.

The term "computer-usable medium," as used herein, refers to any medium that provides information or is usable by the processor(s) 507. Such a medium can take many forms, including, but not limited to, non-volatile, volatile and transmission media. Non-volatile media, i.e., media that can retain information in the absence of power, includes the ROM 509, CD ROM, magnetic tape, and magnetic discs. Volatile media, i.e., media that can not retain information in the absence of power, includes the main memory 508. Transmission media includes coaxial cables, copper wire and fiber optics, including the wires that comprise the bus 506. Transmission media can also take the form of carrier waves; i.e., electromagnetic waves that can be modulated, as in frequency, amplitude or phase, to transmit information signals. Additionally, transmission media can take the form of acoustic or light waves, such as those generated during radio wave and infrared data communications.

In the foregoing specification, the embodiments have been described with reference to specific elements thereof. It will, however, be evident that various modifications and changes can be made thereto without departing from the broader spirit and scope of the embodiments. For example, the reader is to understand that the specific ordering and combination of process actions shown in the process flow diagrams described herein is merely illustrative, and that using different or additional process actions, or a different combination or ordering of process actions can be used to enact the embodiments. The specification and drawings are, accordingly, to be regarded in an illustrative rather than restrictive sense.

It should also be noted that the present invention can be implemented in a variety of computer systems. The various techniques described herein can be implemented in hardware or software, or a combination of both. Preferably, the techniques are implemented in computer programs executing on programmable computers that each include a processor, a storage medium readable by the processor (including volatile and non-volatile memory and/or storage elements), at least one input device, and at least one output device. Program code is applied to data entered using the input device to perform the functions described above and to generate output information. The output information is applied to one or more output devices. Each program is preferably implemented in a high level procedural or object oriented programming language to communicate with a computer system. However, the programs can be implemented in assembly or machine language, if desired. In any case, the language can be a compiled or interpreted language. Each such computer program is preferably stored on a storage medium or device (e.g., ROM or magnetic disk) that is readable by a general or special purpose programmable computer for configuring and operating the computer when the storage medium or device is read by the computer to perform the procedures described above. The system can also be considered to be implemented as a computer-readable storage medium, configured with a computer program, where the storage medium so configured causes a computer to operate in a specific and predefined manner. Further, the storage elements of the exemplary computing applications can be relational or sequential (flat file) type computing databases that are capable of storing data in various combinations and configurations.

Although exemplary embodiments of the invention have been described in detail above, those skilled in the art will readily appreciate that many additional modifications are possible in the exemplary embodiments without materially departing from the novel teachings and advantages of the invention. Accordingly, these and all such modifications are intended to be included within the scope of this invention construed in breadth and scope in accordance with the appended claims.

For example, the configuration and arrangement of the system can be modified. While the figures show recirculation of the water from the lower region to the upper region of the tank, the recirculation can occur generally between a first region and a second region of an enclosure. A liquid other than water can be used. Different chemistries, process parameters, and process conditions can be used and optimized for treating different contaminants and producing the desired ozonated water for different applications. The scope of the invention should, therefore, be determined not with reference to the above description, but instead should be determined with reference to the appended claims along with their full scope of equivalents.

The invention claimed is:

1. A method of dissolving ozone in a liquid, comprising the steps of:
   introducing ozone into a flow of a liquid in a pipe into a tank;
   recirculating at least a portion of the liquid from the tank via the pipe and a pump coupled with the pipe and a liquid inlet;
   delivering the recirculated liquid into an upper region of the tank; and,
   releasing the liquid from the tank, thereby depressurizing the liquid and providing for at least some of the ozone to emerge from the liquid as gas bubbles.

2. The method of claim 1:
   wherein the ozone is introduced into the flow of the liquid via a venturi inlet, and, the venturi inlet is on the pipe.

3. The method of claim 2, further comprising the step of:
   pumping the flow of the liquid at a sufficient pressure, thereby producing a vacuum at the venturi inlet;
   wherein the vacuum is sufficient to draw at least some of the ozone into the pipe.

4. The method of claim 3 further comprising the step of:
   providing a release rate for releasing the liquid from the tank;
   wherein the liquid is recirculated at a recirculation rate within a range of 1 to 6 times the release rate.

5. The method of claim 1 further comprising the steps of:
   measuring dissolved ozone within the tank, thereby providing a measurement;
   providing a control signal responsive to the measurement; and,
   generating the ozone responsive to the control signal.

6. A method of dissolving ozone in a liquid, comprising the steps of:
   providing a flow of a liquid in a pipe into a tank;
   introducing ozone into the flow of the liquid via a venturi inlet, wherein the venturi inlet is on the pipe;
   pumping the flow of the liquid at a sufficient pressure, thereby producing a vacuum at the venturi inlet; and,
   recirculating at least a portion of the liquid from the tank via the pipe into an upper region of the tank;
   wherein the vacuum is sufficient to draw at least some of the ozone into the pipe.

7. The method of claim 6, further comprising the step of:
   receiving the flow of the liquid into the tank at a distance from an exit outlet, thereby providing a contact time for dissolving ozone in the liquid and degassing the liquid.

8. The method of claim 6 further comprising the steps of:
   measuring dissolved ozone within the tank, thereby providing a measurement;
   providing a control signal responsive to the measurement; and,
   generating the ozone responsive to the control signal.

* * * * *